United States Patent
LaRose et al.

(10) Patent No.: US 10,117,981 B2
(45) Date of Patent: Nov. 6, 2018

(54) PLATINUM-COBALT-BORON BLOOD PUMP ELEMENT

(71) Applicant: HeartWare, Inc., Miami Lakes, FL (US)

(72) Inventors: Jeffrey A. LaRose, Parkland, FL (US); Charles R. Shambaugh, Jr., Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 366 days.

(21) Appl. No.: 13/621,551

(22) Filed: Sep. 17, 2012

(65) Prior Publication Data

US 2014/0079557 A1    Mar. 20, 2014
US 2014/0322022 A9    Oct. 30, 2014

Related U.S. Application Data

(63) Continuation of application No. 12/322,821, filed on Feb. 6, 2009, now abandoned.

(60) Provisional application No. 61/069,698, filed on Mar. 17, 2008, provisional application No. 61/065,141, filed on Feb. 8, 2008.

(51) Int. Cl.
| | |
|---|---|
| *A61M 1/10* | (2006.01) |
| *F04D 29/02* | (2006.01) |
| *F04D 29/18* | (2006.01) |
| *A61M 1/12* | (2006.01) |

(52) U.S. Cl.
CPC ........ *A61M 1/1015* (2014.02); *A61M 1/1029* (2014.02); *A61M 1/125* (2014.02); *F04D 29/026* (2013.01); *F04D 29/181* (2013.01); *A61M 1/101* (2013.01); *A61M 1/1012* (2014.02); *A61M 1/1017* (2014.02); *A61M 1/1031* (2014.02); *A61M 1/122* (2014.02); *A61M 2205/02* (2013.01); *F05D 2300/11* (2013.01); *F05D 2300/143* (2013.01); *F05D 2300/17* (2013.01); *F05D 2300/507* (2013.01)

(58) Field of Classification Search
CPC ...... F04D 3/00; F04D 13/0606; F04D 29/026; F04D 29/048; F04D 29/181; A61M 1/1015; A61M 1/1036
USPC ..................... 417/356, 423.1; 415/900, 200; 416/241 R; 604/151
See application file for complete search history.

(56) References Cited

U.S. PATENT DOCUMENTS

| | | | | |
|---|---|---|---|---|
| 1,755,321 | A | * | 4/1930 | Hendrickson ............. B23P 6/00 29/889.1 |
| 3,608,088 | A | * | 9/1971 | Dorman ....................... 623/3.13 |

(Continued)

FOREIGN PATENT DOCUMENTS

| | | |
|---|---|---|
| WO | 2007040663 | 4/2007 |
| WO | 2009099644 A1 | 8/2009 |

OTHER PUBLICATIONS

Extended European Search Report for Application No. EP09708643 dated May 28, 2014.

(Continued)

*Primary Examiner* — Kenneth J Hansen
(74) *Attorney, Agent, or Firm* — Christopher & Weisberg, P.A.

(57) ABSTRACT

A magnetic impeller for a blood pump such as a magnetically driven, rotary ventricular assist device for pumping blood of a patient, the impeller comprising a magnetic alloy including platinum, cobalt, and boron.

28 Claims, 3 Drawing Sheets

(56) References Cited

U.S. PATENT DOCUMENTS

| | | | |
|---|---|---|---|
| 4,983,230 A * | 1/1991 | Overfelt et al. | 148/300 |
| 7,699,586 B2 | 4/2010 | LaRose et al. | |
| 2005/0084398 A1* | 4/2005 | Wampler et al. | 417/423.7 |
| 2006/0122456 A1* | 6/2006 | LaRose et al. | 600/16 |
| 2007/0078293 A1 | 4/2007 | Shambaugh, Jr. et al. | |
| 2008/0269880 A1* | 10/2008 | Jarvik | A61M 1/101 623/3.13 |

OTHER PUBLICATIONS

International Search Report issued by the International Searching Authority (ISA/US) in connection with International Application No. PCT/US09/000775.

Written Opinion of the International Searching Authority issued by the International Searching Authority (ISA/US) in connection with International Application No. PCT/US09/000775.

Office Action dated Oct. 27, 2010 in connection with U.S. Appl. No. 12/322,821, filed Feb. 6, 2009.

Office Action dated Jan. 26, 2011 in connection with U.S. Appl. No. 12/322,821, filed Feb. 6, 2009.

Final Office Action dated Nov. 2, 2011 in connection with U.S. Appl. No. 12/322,821, filed Feb. 6, 2009.

Office Communication dated Jul. 20, 2012 in connection with U.S. Appl. No. 12/322,821, filed Feb. 6, 2009.

* cited by examiner

PLATINUM-COBALT-BORON BLOOD PUMP ELEMENT

CROSS-REFERENCE TO RELATED APPLICATION

This application is a continuation of U.S. Ser. No. 12/322,821, filed Feb. 6, 2009, which claims the benefit of U.S. Provisional Patent Application Nos. 61/069,698, filed Mar. 17, 2008, and 61/065,141, filed Feb. 8, 2008, the disclosure of each of which is hereby incorporated by reference into this application.

BACKGROUND OF THE INVENTION

The present invention relates to an impeller comprising an alloy including effective amounts of platinum, cobalt, and boron for use in a blood pump such as a rotary Ventricular Assist Device ("VAD").

Clinical applications of Ventricular Assist Devices ("VADs") to support patients with end-stage heart disease, as a bridge to cardiac transplantation, or as an end stage therapeutic modality have become an accepted clinical practice in cardiovascular medicine. It is estimated that greater than 35,000 persons suffering from end stage cardiac failure are candidates for cardiac support therapy.

VADs may utilize a blood pump for imparting momentum to a patient's blood thereby driving the blood to a higher pressure. In particular, a rotary VAD is a blood pump containing an electromagnetically coupled impeller that spins to assist the patient's circulatory system.

U.S. patent application Ser. No. 12/072,471, filed Feb. 26, 2008, the disclosure of which is hereby incorporated by reference into this application, provides an example of an intravascular rotary VAD that may be implanted in the patient to provide assistance in pumping blood for hearts that are afflicted with congestive heart failure or the like. This intravascular rotary VAD is a miniaturized VAD that has many uses due to it's small size. This miniaturization has made possible new techniques for less invasive implantation which in expected to shorten recovery times for patients following surgery.

U.S. Patent Application Publication No. US 2007/0078293 A1, the disclosure of which is hereby incorporated by reference provides an example of a blood pump impeller including a platinum-cobalt alloy that is magnetizable to a high degree and may be manufactured as a single piece.

U.S. Pat. No. 4,983,230, the disclosure of which is hereby incorporated by reference describes a magnetic platinum-cobalt-boron alloy having high coercivity for various uses.

By this invention, an improved blood pump impeller is provided for use in, for example, a rotary VAD. It has been found that an impeller comprising an alloy including predetermined amounts of platinum, cobalt, and boron results in an impeller that is highly effective and has superior magnetic, mechanical, and biocompatible properties. These superior properties make possible further miniaturization and streamlining of a VAD pump than has previously been impossible in the VAD industry.

BRIEF SUMMARY OF THE INVENTION

One aspect of the invention provides a magnetic impeller for a blood pump, such as, for example, a rotary VAD. The magnetic impeller for a blood pump according to this aspect of the invention preferably comprises a magnetic alloy including platinum, cobalt, and boron. More preferably, the magnetic impeller comprises an alloy consisting essentially of about 12-14 atomic percent of boron, and platinum and cobalt in a platinum-to-cobalt atomic percent ratio of 0.90 to 1.2. Most preferably, the magnetic impeller comprises a magnetic alloy consisting essentially of about 13 atomic percent of boron, 42 atomic percent of platinum, and 45 atomic percent of cobalt.

Another aspect of the invention provides a magnetically driven, implantable, rotary ventricular assist device for pumping blood of a patient. The ventricular assist device according to this aspect of the invention has an impeller comprising a magnetic alloy including platinum, cobalt, and boron. Preferably, the impeller of the ventricular assist device comprises a unitary single body and has a biocompatible blood-contacting surface including a magnetic alloy consisting essentially of platinum, cobalt, and boron. More preferably, the impeller comprises an alloy consisting essentially of about 12-14 atomic percent of boron, and platinum and cobalt in a platinum-to-cobalt atomic percent ratio of 0.90 to 1.2. Most preferably, the magnetic impeller comprises a magnetic alloy consisting essentially of about 13 atomic percent of boron, 42 atomic percent of platinum, and 45 atomic percent of cobalt.

The increased magnetic properties of an impeller consisting essentially of about 13 atomic percent of boron, 42 atomic percent of platinum, and 45 atomic percent of cobalt or an impeller consisting essentially of platinum and cobalt, leads to greater efficiencies between the rotor and the stator. These efficiencies lead to further miniaturization which is medically advantageous.

BRIEF DESCRIPTION OF THE DRAWINGS

For a further understanding of the present invention, reference may be had to the accompanying drawings from which the nature and attendant advantages of the invention will be readily understood, and in which.

DETAILED DESCRIPTION

Figure 1:
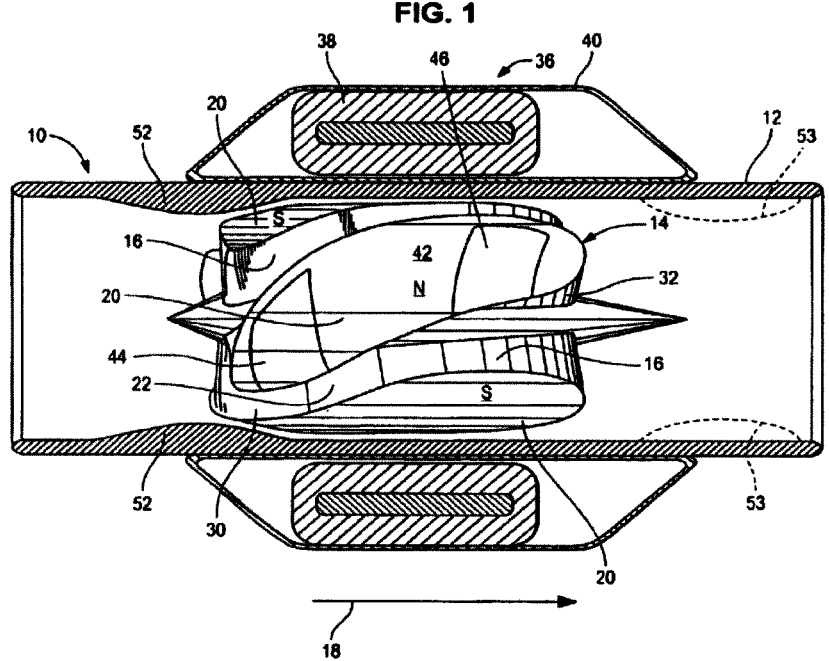
FIG. 1 illustrates an enlarged longitudinal sectional view of an implantable sealed rotary blood pump in accordance with one embodiment of the invention.
Figure 2:
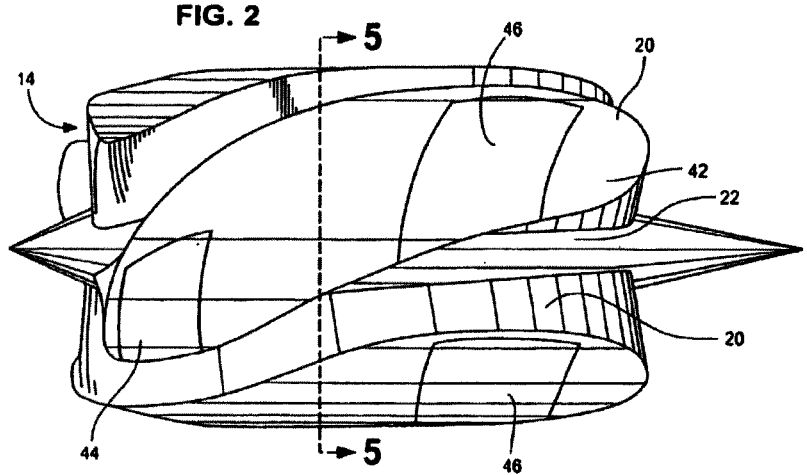
FIG. 2 is an enlarged perspective view of the rotary impeller of the pump of FIG. 1.
Figure 3:
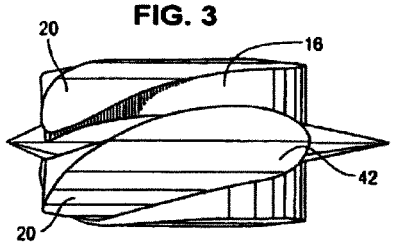
FIGS. 3 and 4 are additional side views of the impeller of FIG. 2 in differing positions.

In describing the embodiments of the present invention illustrated in the drawings, specific terminology is employed for sake of clarity. However, the present disclosure is not intended to be limited to the specific terminology so selected, and it is to be understood that each specific element includes all technical equivalents that operate in a similar manner.

Referring to FIGS. 1-5, an impeller or rotor 14 in accordance with various embodiments of the present invention is disclosed. An "impeller" is defined as the movable, fluid driving portion of a pump. As seen in FIG. 1, impeller 14 may be positioned in an axial-flow rotary VAD pump 10.

In one embodiment, impeller 14 comprises an alloy including platinum, cobalt, and boron. More preferably, the alloy comprises 12-14 atomic percent of boron, together with amounts of platinum and cobalt such that the atomic percent ratio of platinum to cobalt is from 0.90 to 1.2. In a preferred embodiment, the amount of platinum is slightly less than the amount of cobalt. Most preferably, the alloy consists essentially of platinum, cobalt and boron. For example, the alloy may include about 42 atomic percent platinum, 45 atomic percent of cobalt, and 13 atomic percent of boron.

As disclosed in U.S. Pat. No. 4,983,230, the platinum, cobalt, and boron alloy may be formed by rapid solidification of a homogeneous melt of platinum, cobalt and boron. As further disclosed therein, the rapid solidification of a homogenous melt of platinum, cobalt and boron and heat-treatment of the solidified alloy can produce intrinsic coercivities in the range of 12-14 KOe for alloys containing 12-14 atomic percent boron and platinum to cobalt atomic ratio of 0.90 to 1.1. Additionally, the alloy disclosed herein is biocompatible and has high resistance to corrosion, making it suitable for being in contact with blood. Furthermore, as the alloy described above is magnetically isotropic, the alloy can be highly magnetized with a plurality of magnetic poles in any geometric orientation. Further still, the alloy typically has Rockwell hardness on the order of 31 Rc, which eliminates the need for a hard, outer coating. As a result of the foregoing advantages, an efficient and compact VAD design can be achieved which eliminates the need to build conventional assemblies of magnets and support structures, thus decreasing manufacturing costs. Further, by eliminating the need for conventional assemblies and support structures, we further increase the potential for miniaturization.

The entire impeller 14 may be formed by machining from a single solidified piece of the alloy, which may then be magnetized in the desired pole pattern. Preferably, impeller 14 is formed as unitary single piece comprising the above described alloy, which can be fabricated into complex shapes using conventional metal working methods, unlike other "high strength" permanent magnets used in conventional rotary VADs. The use of a single piece impeller eliminates assembly procedures and hermeticity concerns which are associated with a traditional approach of placing magnetic materials within an impeller casing and laser welding closure caps to the casing. The single piece impeller may entirely consist of the biocompatible alloy essentially consisting of platinum, cobalt, and boron, thus ensuring that the entire impeller, including both the outer surface and the interior of the impeller, is biocompatible and suitable for contact with the blood.

Figure 4:
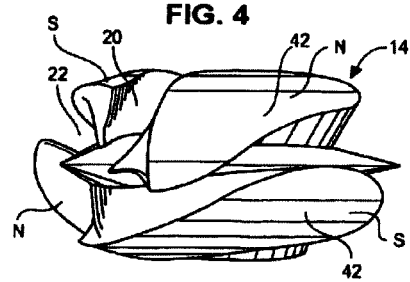

Impeller 14 may be magnetized with the North (N) and South (S) magnetic poles being as indicated on bladelike projections 20 (FIG. 4).

The impeller 14 disclosed in FIGS. 1-5 may operate in a VAD 10 (FIG. 1) as described below.

Impeller or rotor 14 may be positioned within the lumen of pump housing 12 and may have a hydrodynamic surface (specifically a series of hydrodynamic surfaces 16 that tend to propel blood in an axial direction as indicated by arrow 18) as impeller 14 is rotated clockwise. Blood pump 10 may be connected to the patient's vascular system to serve as a rotary VAD.

As illustrated in FIG. 1, impeller 14 may comprise blade-like projections 20 that extend radially outward and have walls 16 that define generally longitudinally extending spaces 22 between the projections 20. The projections 20 and their side walls 16 constituting the hydrodynamic surfaces may be shaped to form curves in the longitudinally extending spaces 22 which are of a shape tending to drive blood in axial direction 18 as impeller 14 is rotated (clockwise in the embodiment depicted in FIG. 1).

Figure 5:
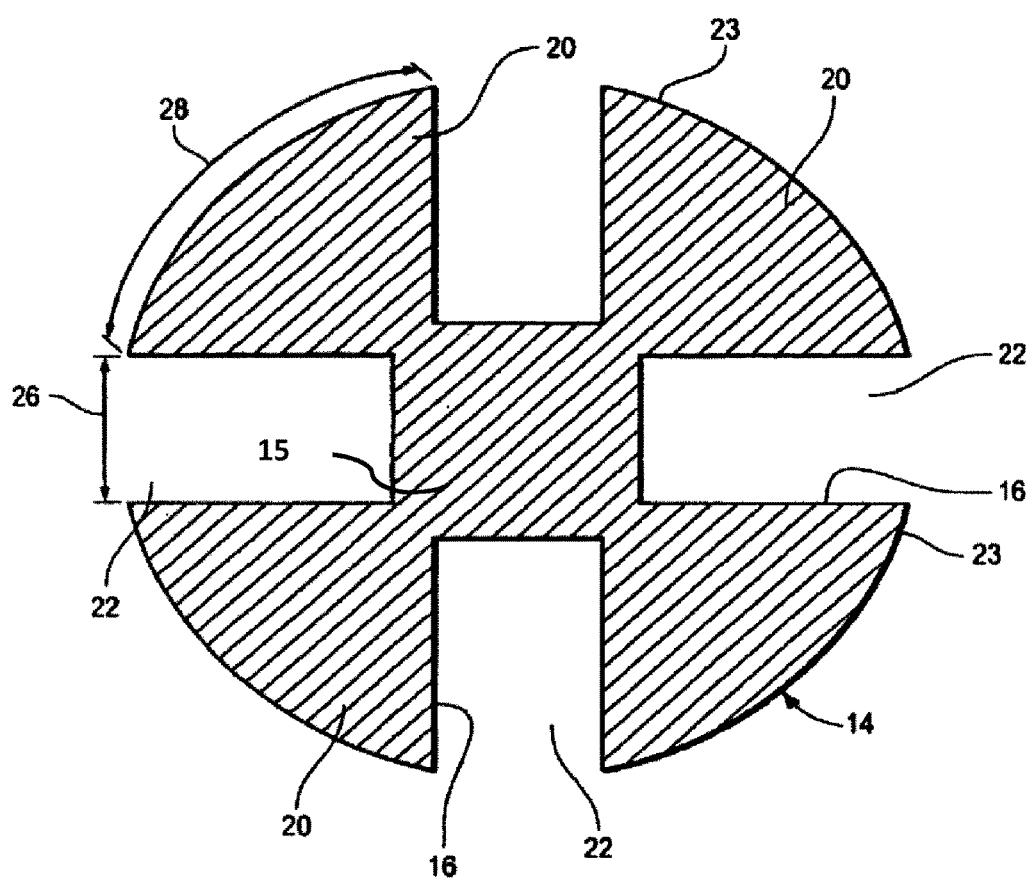
FIG. 5 is a sectional view taken along line 5-5 of FIG. 2.

As can be seen from FIG. 5, the longitudinally extending spaces 22 collectively may have a total circumferential width that is substantially less than the total circumferential width of the collective projections 20. As illustrated in FIG. 5, each of the longitudinally extending spaces 22 has a circumferential or peripheral width 26. The four peripheral widths 26 of the four longitudinally extending spaces 22 together comprise a total peripheral width of all longitudinally extending spaces 22. Similarly, the distance of arc 28 represents the circumferential or peripheral width of the blade-like projection 20. The total collective peripheral width of the longitudinally extending spaces 22 is substantially less than the total collective peripheral width of the respective bladelike projections 20.

Preferably, the transverse sections of longitudinally extending spaces 22 have generally parallel side walls 16, although it can also be seen from FIG. 1 and other drawings that the overall width of longitudinally extending spaces 22 may vary along their lengths, being somewhat narrower at upstream areas 30, and wider at downstream areas 32, as shown in FIG. 1. Clockwise rotation of rotor 14 will result in a flow of blood within the lumen of housing 12 from left to right in direction 18.

Blood pump 10 may further comprise a motor stator 36 (FIG. 1) that includes an electrically conductive coil 38 within an enclosure 40 surrounding housing 12 and impeller or rotor 14. The electromagnetic stator 36 serves to rotate impeller 14 by the conventional application of electric power to coil 38, which is converted to a magnetic field that causes the impeller 14 to rotate either clockwise or counterclockwise depending on the polarity of the electric power. The specific technology for accomplishing this may be similar to that which is well known in the prior art.

FIGS. 1-4 show radially outer faces 42 of bladelike projections 20 and also show a pair of hydrodynamic bearings 44, 46, which may be defined on projections 20 in the embodiment of FIGS. 1-5, and which use fluid pressure to cause impeller 14 to be centered in the lumen of tubular housing 12 as the impeller 14 rotates without the need for physical bearings utilizing rubbing, solid surfaces.

Thus, impeller 14 may rotate being held away from the inner wall of housing 12 by hydrodynamic bearings 44, 46 on each of the blade-like projections 20. At the rear of impeller 14, an inner, annular ring 52 of housing 12 (FIG. 1) may project inwardly from the inner wall cylinder housing 12 to limit the leftward motion of rotor 14. Ring 52 may comprise an annular series of spaced projections, or it may comprise a solid ring with hydrodynamic bearings 44 serving to prevent contact between rotor 14 and ring 52 as the pump is operating with clockwise rotation of rotor 14. A similar, annular ring 53 may be defined near the other end of housing 12 for similar purpose.

Each of thrust bearings 44, 46 may define a recessed curved outer surface which forms a recessed end portion relative to the outer face 42 of each projection 20 located at the forward end of each bearing 44, 46 from the viewpoint of the (clockwise) spin of the rotor 14a, so that the recessed end forms a leading edge of rotation. The recessed surface may taper in a gradual, curved manner outwardly to the rear end of each thrust bearing 44, 46, at which point, the bearing surface is not recessed, or only very slightly recessed, in a manner similar to that described in U.S. Pat. No. 6,234,772.

Thus, as the impeller 14 rotates, the respective thrust bearings 44 and 46 on each blade-like projection 20 scoop blood into a cross-sectional, recessed area of each bearing that decreases going from end to end, the effect of this being to pressurize the blood, and to thus repel each projection 20 from the inner wall of housing 12 as the impeller 14 rotates. Since the impeller 14 is spaced from the walls of housing 12, the pressurized blood is released out of each bearing by passing across the end and out the sides of the recess. A pressure relief zone is provided at the trailing rotary end of each rotating projection 20.

In one embodiment, stator 36 may comprise a separate hermetically-sealed coil-motor that slides over tubular housing 12 in position, and is secured thereto. Alternatively, stator 36 and coil 38 may be integrally attached to housing 12.

In one embodiment, the stator may be reduced to one-half of the width necessary. This decrease in diameter increases the methods by which a VAD may be implanted into the body. Previously, the intravascular VADs of our earlier application has a diameter of ⅜ of an inch (or approximately 9.525 mm). Using an impeller of the current invention, the outer diameter of the VAD is 25 percent smaller than the device of the earlier application (or approximately 7.14 mm). This decrease in outer diameter made possible by the current invention will lead to less invasive surgical implantation techniques and consequently shorter recovery times for patients.

To provide a further example, the VAD 10 disclosed herein in FIGS. 1-5 is similar, but for the improvements disclosed herein, to that disclosed in U.S. patent application Ser. No. 11/003,810, filed Dec. 3, 2004, the disclosure of which is hereby incorporated by reference herein. Accordingly, VAD 10 may be a single stage, axial blood pump that is a cylindrical device having an outer diameter that is 25 percent smaller than the ten millimeters outer diameter described in (col. 5, 1.12-19) of the '810 application (or 7.5 mm). Alternatively, VAD 10 may have a multistage configuration, wherein multiple blood pumps are connected in series. In this alternative embodiment, VAD 10 may have an outer diameter that is 25 percent smaller than the six millimeter outer diameter described in (col. 6, 1.17-25) of the '810 application (or 4.5 mm).

In the embodiments discussed above, the impeller 14 is formed entirely as a unitary single body comprising the biocompatible platinum, cobalt, and boron alloy. However, this is not essential. For example, impeller 14 may include a non-unitary body formed from a combination of the biocompatible platinum, cobalt, and boron alloy disclosed herein, and other materials. For example, ferromagnetic material such as iron or an iron-nickel alloy, which has desirable ferromagnetic properties, but which is not compatible with blood, may be included in the interior portion 15 of the impeller 14, as outlined in the alternative by the exemplary dashed line in FIG. 5. Although depicted as circular, interior portion 15 may include any portion of impeller 14 located inside of an outer, blood contacting surface 23. Some, or preferably all, of the outer, blood-contacting surfaces 23 of such an impeller 14, including both biocompatible and non-biocompatible body portions, may be defined by the biocompatible alloy including platinum, cobalt, and boron described above, thus ensuring that the blood-contacting surfaces 23 of the impeller are biocompatible.

It is contemplated that the impeller comprising the alloy disclosed herein may be designed to rotate in the counter-clockwise direction, making use of the principles and advantages described above.

It is further contemplated that an impeller comprising the platinum, cobalt, and boron alloy disclosed herein, may be designed for use in both mixed-flow and centrifugal-flow ventricular assist devices, making use of the principles and advantages described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A rotatable impeller for assisting blood flow within a patient's vascular system, the impeller being magnetically driven and including a non-unitary body having an exterior layer and an interior portion opposite the exterior layer, the impeller being configured to be disposed within a housing including an outer diameter of between approximately 4.5 mm to 7.5 mm and having:
   at least one blade-like projection including:
      a first blood contacting surface comprising a biocompatible magnetic alloy including platinum, cobalt and boron, the first blood contacting surface forming a biocompatible surface area defining an entire magnetic and blood-contacting surface of the impeller.

2. The rotatable impeller of claim 1, in which the biocompatible surface area comprises the exterior layer of the impeller and the first blood contacting surface is formed solely from the predetermined biocompatible alloy.

3. The rotatable impeller of claim 2, in which the predetermined biocompatible alloy consists essentially only of platinum, cobalt, and boron.

4. The rotatable impeller of claim 3, in which the predetermined biocompatible alloy comprises about 12 to 14 atomic percent of boron.

5. The rotatable impeller of claim 3, in which the predetermined biocompatible alloy comprises about 12 to 14 atomic percent of boron, and includes amounts of platinum and cobalt in a platinum-to-cobalt atomic percent ratio of 0.90 to 1.1 or to 1.2.

6. The rotatable impeller of claim 3, in which the predetermined biocompatible alloy comprises about 13 atomic percent of boron, 42 atomic percent of platinum, and 45 atomic percent of cobalt.

7. The rotatable impeller of claim 4, in which the predetermined biocompatible alloy has a coercivity range of 12 kOe to 14 kOe.

8. The rotatable impeller of claim 3, in which the biocompatible surface area comprises a plurality of magnetic poles.

9. The rotatable impeller of claim 8, further comprising an electromagnetic stator constructed and arranged to provide a magnetic field for spinning the impeller about an axis.

10. The rotatable impeller of claim 1, in which the first blood contacting surface of the biocompatible surface area of the at least one blade-like projection defines a plurality of projections, each of the projections separated by longitudinal blood flow spaces, each blood flow space having an inlet portion and an outlet portion substantially wider than the inlet portion.

11. The rotatable impeller of claim 10, in which the inlet and outlet portions of each of the longitudinal blood flow spaces communicate with a circumferentially curved blood flow portion therebetween.

12. The rotatable impeller of claim 2, in which the interior portion includes a ferromagnetic material.

13. The rotatable impeller of claim 12, in which the ferromagnetic material comprises iron.

14. The rotatable impeller of claim 13, in which the ferromagnetic material comprises an alloy of iron and nickel.

15. A rotatable impeller configured to be disposed within a housing including an outer diameter of between approximately 4.5 mm to 7.5 mm for assisting blood flow within a patient's vascular system, the impeller comprising:
a non-unitary body having an exterior layer and an interior portion opposite the exterior layer, the non-unitary body having at least one blade-like projection including:
a first blood contacting surface formed entirely from a magnetic biocompatible alloy including platinum, cobalt and boron, and defining an entire magnetic and blood-contacting surface of the impeller, wherein the impeller is electromagnetically coupled to rotate within a ventricular assist device.

16. The rotatable impeller of claim 15, in which the predetermined biocompatible alloy consists only of platinum, cobalt, and boron and the first blood contacting surface of the impeller is formed as a single piece of the predetermined biocompatible alloy.

17. The rotatable impeller of claim 16, wherein the at least one blade-like projection having the first blood contacting surface of the impeller comprises a plurality of projections separated by a plurality of longitudinal blood flow spaces, each blood flow space having an inlet portion and an outlet portion substantially wider than the inlet portion.

18. The rotatable impeller of claim 17, in which the inlet and outlet portions of each of the longitudinal blood flow spaces communicates with a circumferentially curved blood flow portion therebetween.

19. The rotatable impeller of claim 15, in which, the exterior layer defines the entire blood contacting surface of the impeller.

20. The rotatable impeller of claim 19, in which the first blood contacting surface of the exterior layer consists only of platinum, cobalt, and boron.

21. The rotatable impeller of claim 15, in which the ventricular assist device is a single stage axial blood pump.

22. The rotatable impeller of claim 21, in which the housing is a cylindrical housing with an outer diameter of approximately 7.14 mm.

23. The rotatable impeller of claim 22, in which the outer diameter of the cylindrical housing is between 7.14 mm and 7.5 mm.

24. The rotatable impeller of claim 21, in which the ventricular assist device is comprised of a plurality of blood pumps connected in series, each blood pump having a cylindrical housing with an outer diameter of approximately 4.5 mm.

25. A rotatable impeller configured to be disposed within a housing including an outer diameter of between approximately 4.5 mm to 7.5 mm for assisting blood flow within a patient's vascular system, the impeller being magnetically driven and having:
a non-unitary body comprising:
a first portion formed entirely of a magnetic biocompatible alloy including platinum, cobalt, and boron, the first portion including a plurality of projections defining a plurality of longitudinal blood flow spaces therebetween;
a blood contacting surface formed entirely by the first portion of the non-unitary body; and
an interior portion surrounded entirely by the blood contacting surface.

26. The rotatable impeller of claim 25, wherein the interior portion is comprised of a non-biocompatible material.

27. The rotatable impeller of claim 25, wherein each longitudinal blood flow space includes an inlet portion and an outlet portion substantially wider than the inlet portion.

28. The rotatable impeller of claim 27, in which the inlet and outlet portions of each of the longitudinal blood flow spaces communicates with a circumferentially curved blood flow portion therebetween.

* * * * *